United States Patent
Benson et al.

(10) Patent No.: US 10,085,834 B2
(45) Date of Patent: Oct. 2, 2018

(54) MITRAL VALVE REPLACEMENT TOGGLE CELL SECUREMENT

(71) Applicant: St. Jude Medical, Cardiology Division, Inc., St. Paul, MN (US)

(72) Inventors: Thomas Mark Benson, Minneapolis, MN (US); Tracee Eidenschink, Wayzata, MN (US)

(73) Assignee: St. Jude Medical, Cardiology Divsion, Inc., St. Paul, MN (US)

( * ) Notice: Subject to any disclaimer, the term of this patent is extended or adjusted under 35 U.S.C. 154(b) by 0 days.

(21) Appl. No.: 15/125,356

(22) PCT Filed: Mar. 13, 2015

(86) PCT No.: PCT/US2015/020446
§ 371 (c)(1),
(2) Date: Sep. 12, 2016

(87) PCT Pub. No.: WO2015/142648
PCT Pub. Date: Sep. 24, 2015

(65) Prior Publication Data
US 2017/0165054 A1   Jun. 15, 2017

Related U.S. Application Data

(60) Provisional application No. 61/954,810, filed on Mar. 18, 2014.

(51) Int. Cl.
*A61F 2/24* (2006.01)

(52) U.S. Cl.
CPC .............. *A61F 2/24* (2013.01); *A61F 2/2418* (2013.01); *A61F 2/2427* (2013.01); *A61F 2220/0008* (2013.01)

(58) Field of Classification Search
CPC ........................................................ A61F 2/06
(Continued)

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 198 57 887 A1 | 7/2000 |
| DE | 101 21 210 A1 | 11/2002 |

(Continued)

OTHER PUBLICATIONS

"Closed heart surgery: Back to the future", Samuel V. Lichtenstein, The Journal of Thoracic and Cardiovascular Surgery, vol. 131, No. 5, pp. 941-943.

(Continued)

*Primary Examiner* — Yashita Sharma
(74) *Attorney, Agent, or Firm* — Lerner, David, Littenberg, Krumholz & Mentlik, LLP

(57) ABSTRACT

A collapsible and expandable stent (320) extends in an axial direction from a proximal end to a distal end. The stent may include a plurality of first cells (324), each first cell having an open space defined by a first plurality of struts (322). The stent may further include a second cell (330) nested in the open space of one of the first cells, the second cell being defined by a second plurality of struts (330a-d). The stent may additionally include first and second connecting struts (332, 334) connecting the second cell to the one first cell. The second cell may be configured to pivot about the first and second connecting struts with respect to the one first cell. The pivoting may create a clearance space between the second cell and an outer perimeter of the stent in which portions of a native valve structure may be clamped.

11 Claims, 13 Drawing Sheets

(58) Field of Classification Search
USPC .................................................. 623/1.1–2.38
See application file for complete search history.

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,685,086 B2 * | 4/2014 | Navia .................. | A61F 2/2418 623/2.14 |
| 8,840,663 B2 | 9/2014 | Salahieh et al. | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0114912 A1 * | 6/2003 | Sequin .................... | A61F 2/856 623/1.11 |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |

(56) References Cited

U.S. PATENT DOCUMENTS

| | | |
|---|---|---|
| 2011/0029072 A1 | 2/2011 | Gabbay |
| 2012/0303116 A1 | 11/2012 | Gorman, III et al. |

FOREIGN PATENT DOCUMENTS

| | | | |
|---|---|---|---|
| DE | 102005003632 | A1 | 8/2006 |
| DE | 20 2008 009 610 | U1 | 12/2008 |
| EP | 0850607 | A1 | 7/1998 |
| EP | 1 000 590 | A1 | 5/2000 |
| EP | 1 360 942 | A1 | 11/2003 |
| EP | 1 584 306 | A1 | 10/2005 |
| EP | 1 598 031 | A2 | 11/2005 |
| EP | 1926455 | A2 | 6/2008 |
| FR | 2 847 800 | A1 | 6/2004 |
| FR | 2850008 | A1 | 7/2004 |
| WO | 91/17720 | A1 | 11/1991 |
| WO | 97/16133 | A1 | 5/1997 |
| WO | 98/32412 | A2 | 7/1998 |
| WO | 99/13801 | A1 | 3/1999 |
| WO | 01/028459 | A1 | 4/2001 |
| WO | 01/49213 | A2 | 7/2001 |
| WO | 01/054625 | A1 | 8/2001 |
| WO | 01/056500 | A1 | 8/2001 |
| WO | 01/076510 | A2 | 10/2001 |
| WO | 02/36048 | A1 | 5/2002 |
| WO | 02/47575 | A2 | 6/2002 |
| WO | 02067782 | A2 | 9/2002 |
| WO | 03/047468 | A1 | 6/2003 |
| WO | 2005070343 | A1 | 8/2005 |
| WO | 06/073626 | A2 | 7/2006 |
| WO | 07071436 | A2 | 6/2007 |
| WO | 2008002441 | A2 | 1/2008 |
| WO | 08/070797 | A2 | 6/2008 |
| WO | 2007058857 | A2 | 8/2009 |
| WO | 2011029631 | A1 | 8/2009 |
| WO | 10/008548 | A2 | 1/2010 |
| WO | 10/008549 | A1 | 1/2010 |
| WO | 10/096176 | A1 | 8/2010 |
| WO | 10/098857 | A1 | 9/2010 |
| WO | 2011002996 | A2 | 1/2011 |

OTHER PUBLICATIONS

"Direct-Access Valve Replacement", Christoph H. Huber, et al., Journal of the American College of Cardiology, vol. 46, No. 2, (Jul. 19, 2005).
"Minimally invasive cardiac surgery", M. J. Mack, Surgical Endoscopy, 2006, 20:S488-S492, DOI: 10.1007/s00464-006-0110-8 (presented Apr. 24, 2006).
"Percutaneous Aortic Valve Implantation Retrograde From the Femoral Artery", John G. Webb et al., Circulation, 2006; 113:842-850 (Jun. 2, 2006).
"Transapical aortic valve implantation: an animal feasibility study"; Todd M. Dewey et al., The annals of thoracic surgery 2006; 82: 110-6 (Feb. 13, 2006).
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical Transcatheter Aortic Valve Implantation in Humans", Samuel V. Lichtenstein et al., Circulation. 2006; 114: 591-596 (Jul. 31, 2006).
Catheter-implanted prosthetic heart valves, Knudsen, L.L., et al., The International Journal of Artificial Organs, vol. 16, No. 5 1993, pp. 253-262.
Is It Reasonable to Treat All Calcified Stenotic Aortic Valves With a Valved Stent?,579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR.
Textbook "Transcatheter Valve Repair", 2006, pp. 165-186.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.
International Search Report for PCT Application No. PCT/2015/020446; Performed by authorized officer Bronwen Steiner at European Patent Office NL-2280 HV Rijswijk dated Aug. 6, 2015.

\* cited by examiner

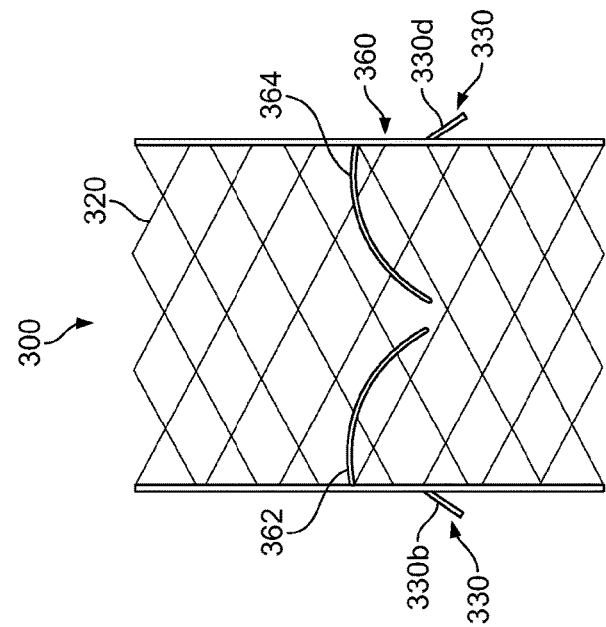
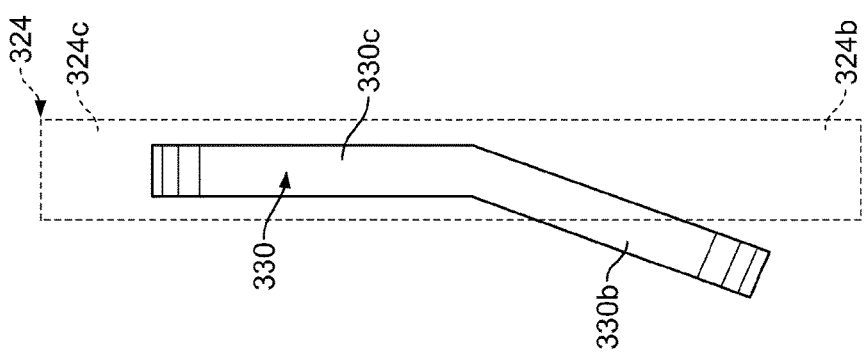

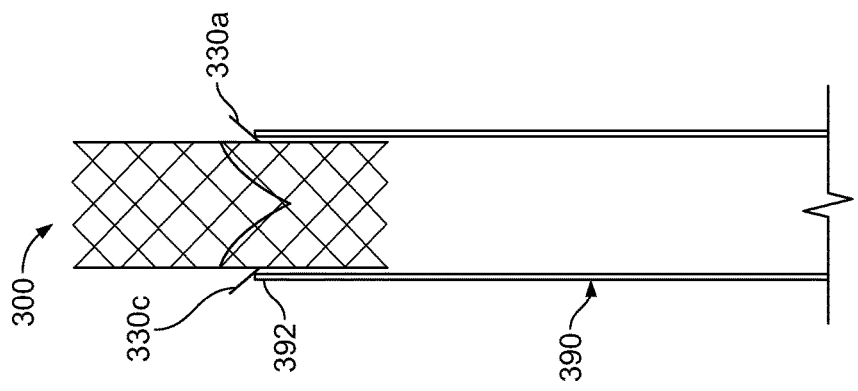
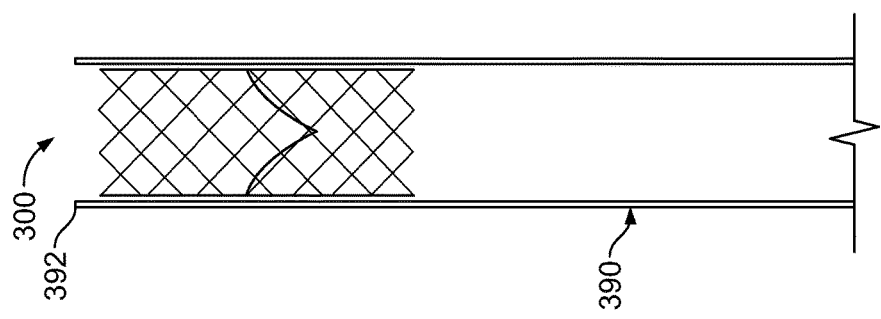

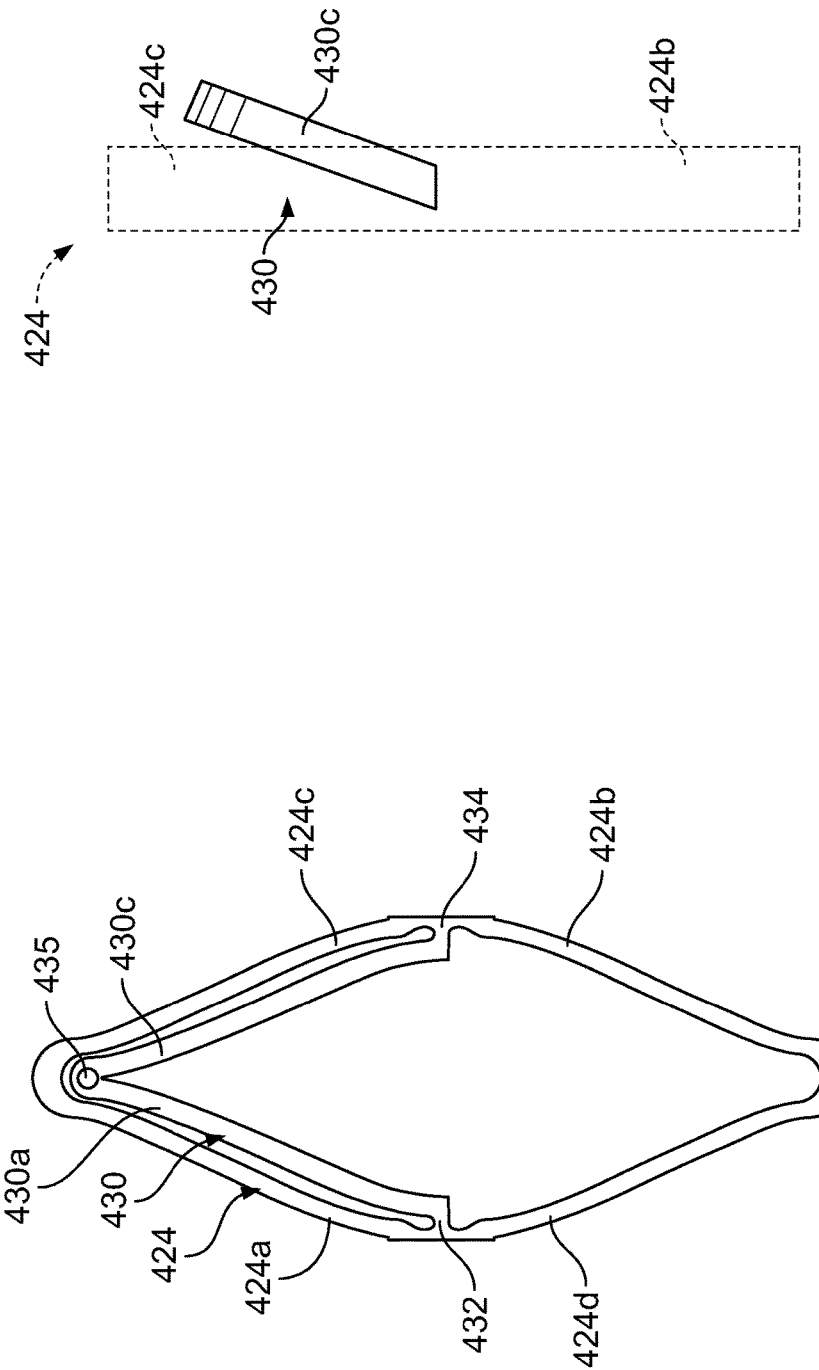

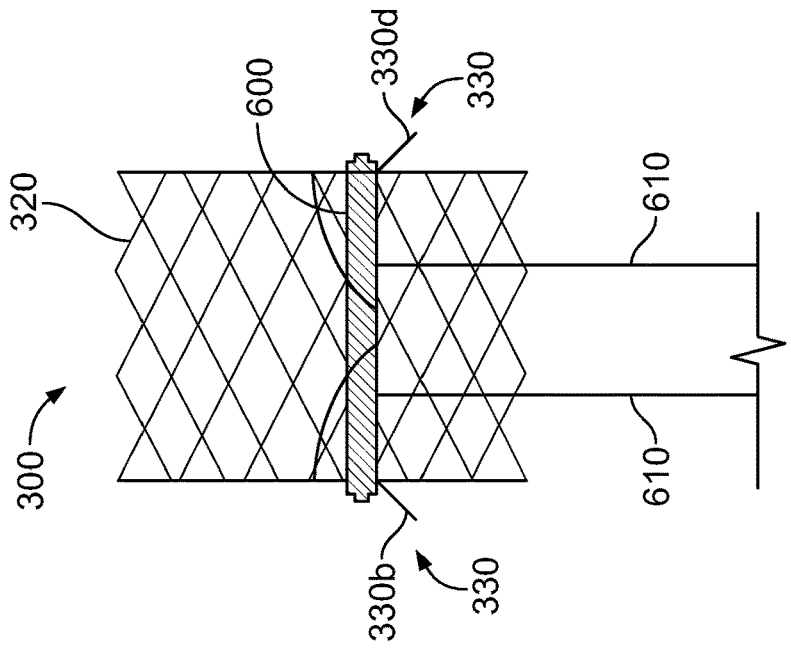
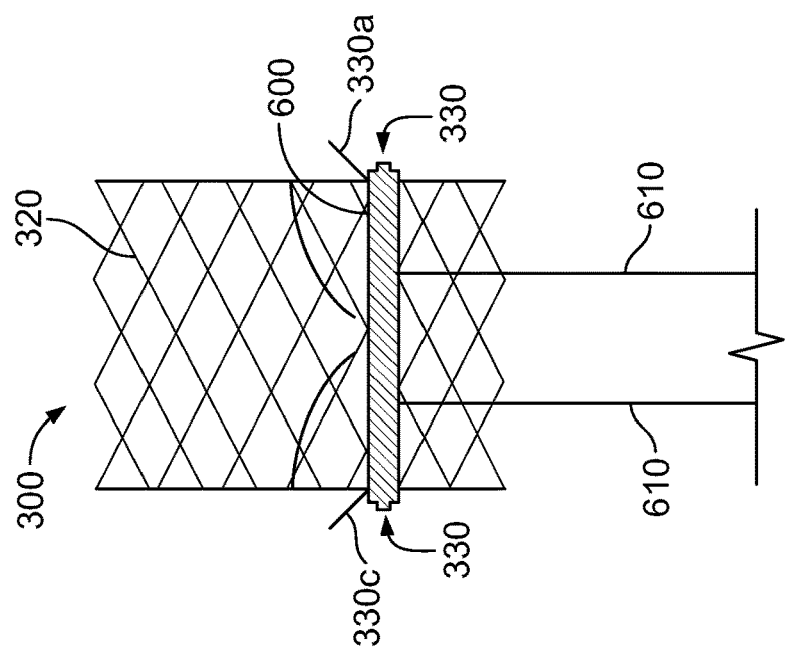

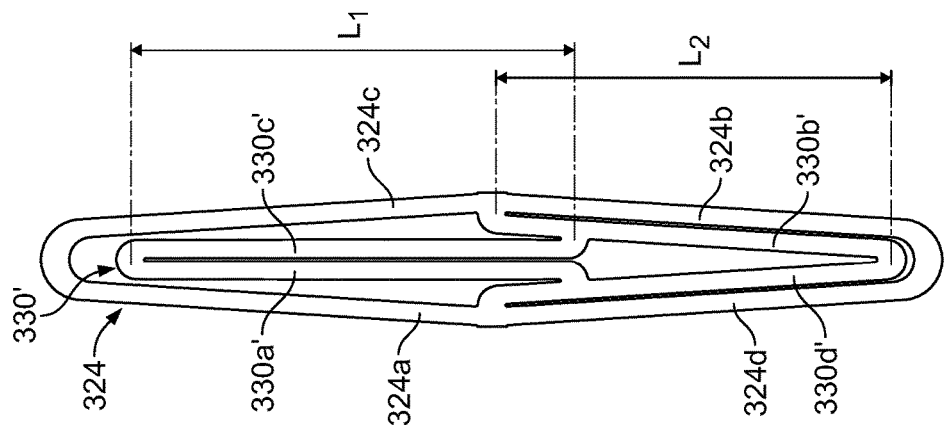
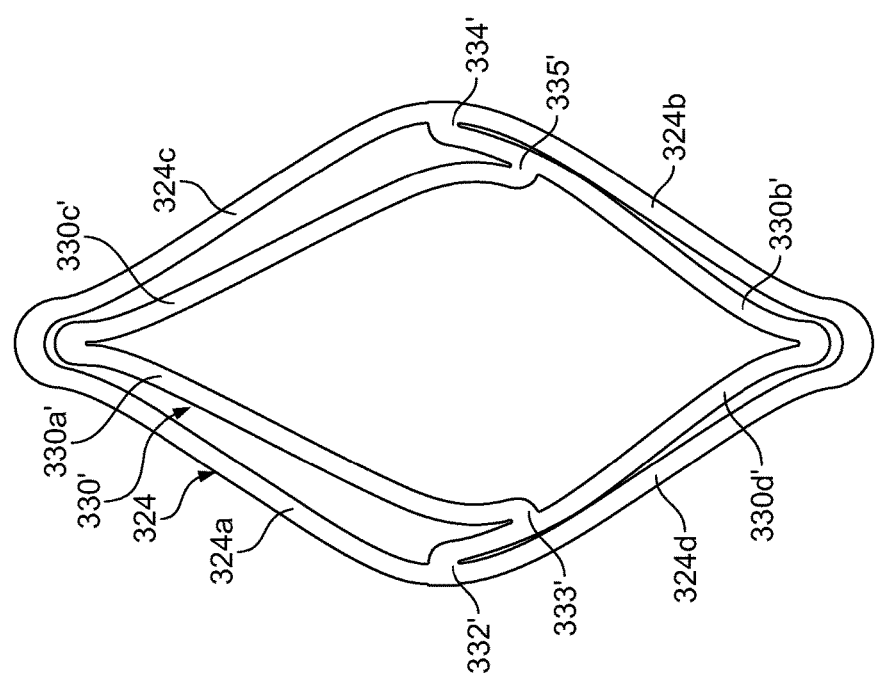
FIG. 8B
FIG. 8A

MITRAL VALVE REPLACEMENT TOGGLE CELL SECUREMENT

CROSS-REFERENCE TO RELATED APPLICATIONS

The present application is a national phase entry under 35 U.S.C. § 371 of International Application No. PCT/US2015/020446, filed Mar. 13, 2015, published in English and which claims the benefit of the filing date of U.S. Provisional Application No. 61/954,810, filed Mar. 18, 2014, entitled "MITRAL VALVE REPLACEMENT TOGGLE CELL SECUREMENT," the disclosures of which are both hereby incorporated by reference herein.

BACKGROUND

The present disclosure relates to heart valve replacement and, in particular, to collapsible prosthetic heart valves. More particularly, the present disclosure relates to devices and methods for securing collapsible prosthetic heart valves within native valve annuluses.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY

According to one embodiment of the disclosure, a collapsible and expandable stent extends in an axial direction from a proximal end to a distal end. The stent may include a plurality of first cells, each first cell having an open space defined by a first plurality of struts. The stent may further include a second cell nested in the open space of one of the first cells, the second cell being defined by a second plurality of struts of the stent. The stent may additionally include first and second connecting struts connecting the second cell to the one of the first cells. The second cell may be configured to pivot about the first and second connecting struts with respect to the one of the first cells.

According to a further embodiment of the disclosure, a method of delivering a prosthetic heart valve into a patient may include providing a delivery device including a sheath extending from a proximal end to a distal end. The method may also include advancing the sheath to an implant site within the patient, the prosthetic heart valve being housed within the sheath in a collapsed condition. The prosthetic heart valve may have a stent extending in an axial direction from a proximal end to a distal end with a plurality of first cells, each first cell having an open space defined by a first plurality of struts, and a second cell nested in the open space of one of the first cells, the second cell being defined by a second plurality of struts. The method may further include retracting the distal end of the sheath with respect to the prosthetic heart valve until at least a portion of the second cell clears the distal end of the sheath. The method may still further include, after at least a portion of the second cell clears the distal end of the sheath, pivoting the second cell with respect to the one of the first cells to create a clearance between the second cell and an outer perimeter of the stent.

BRIEF DESCRIPTION OF THE DRAWINGS

Various embodiments of the present disclosure are described herein with reference to the drawings, wherein:

FIG. 4A is an enlarged isolated side view of the nested cell of FIG. 3B in an expanded condition after being shape-set;

FIG. 4B is a longitudinal cross-section a prosthetic heart valve incorporating a plurality of nested cells of FIG. 4A in an expanded condition;

FIG. 4C is a longitudinal cross-section of the prosthetic heart valve of FIG. 4B being deployed from the delivery device;

FIG. 4D is a longitudinal cross-section of the prosthetic heart valve of FIG. 4B in a collapsed condition partially within a delivery device;

FIG. 5A is an enlarged isolated front view of another embodiment of a nested cell in an expanded condition within another cell of a prosthetic heart valve;

FIG. 5B is an enlarged isolated side view of the nested cell of FIG. 5A in an expanded condition after being shape-set;

FIG. 7A is a longitudinal cross-section a prosthetic heart valve with a resheathing member in a first position;

FIG. 7B is a longitudinal cross-section of the prosthetic heart valve of FIG. 7A with the resheathing member in a second position;

FIG. 8A is an enlarged isolated front view of an embodiment of a nested cell in an expanded condition within another cell of a prosthetic heart valve;

FIG. 8B is an enlarged isolated front view of the nested cell of FIG. 8A within the other cell of the prosthetic heart valve in a collapsed condition;

DETAILED DESCRIPTION

In conventional collapsible heart valves, the stent is usually anchored within the native valve annulus via the radial force exerted by the expanding stent against the native valve annulus. If the radial force is too high, damage may occur to heart tissue. If, instead, the radial force is too low, the heart valve may move from its implanted position. For prosthetic mitral valves, for example, the implanted valve may move into either the left ventricle or the left atrium, requiring emergency surgery to remove the displaced valve. Moreover, in certain applications, such as mitral valve replacement, the heart valve may require a lower profile so as not to interfere with surrounding tissue structures. Such a low profile may make it difficult for the valve to remain in place. Other designs may include hooks or similar features that passively engage tissue until tissue ingrowth is established.

In view of the foregoing, there is a need for further improvements to the devices, systems, and methods for prosthetic heart valve implantation and the anchoring of collapsible prosthetic heart valves, and in particular, self-expanding prosthetic heart valves. Among other advantages, the devices, systems and methods of the present disclosure may address one or more of these needs.

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Further, when used herein with reference to a delivery device, the terms "proximal" and "distal" are to be taken as relative to a user using the device in an intended manner. "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified.

Figure 1:
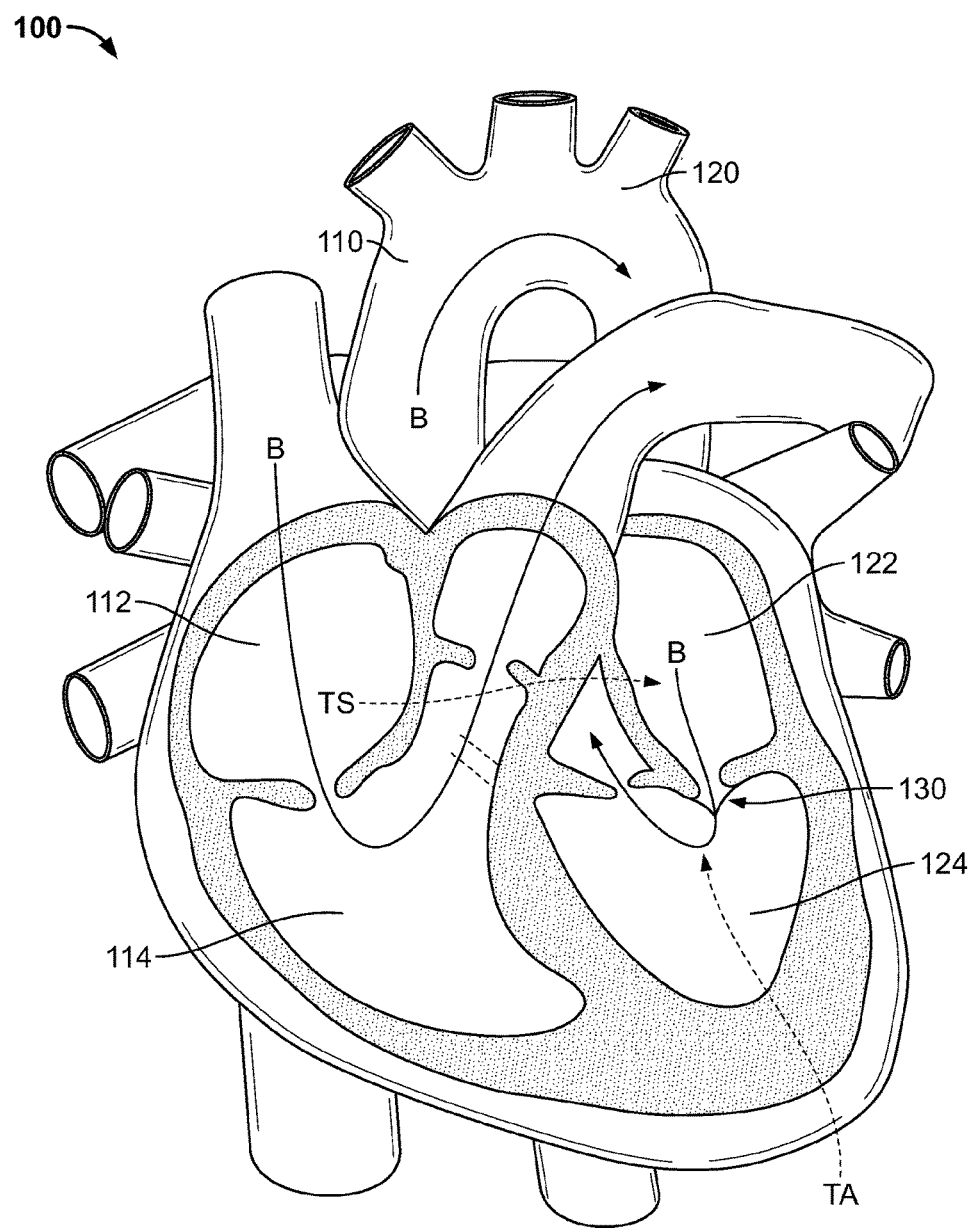
FIG. 1 is a schematic cutaway representation of a human heart showing a transapical delivery approach.

FIG. 1 is a schematic cutaway representation of human heart 100. Heart 100 includes two atria and two ventricles: right atrium 112 and left atrium 122, and right ventricle 114 and left ventricle 124. Heart 100 further includes aorta 110, and aortic arch 120. Disposed between left atrium 122 and left ventricle 124 is mitral valve 130. Mitral valve 130, also known as the bicuspid valve or left atrioventricular valve, is a dual-flap that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled "TA", indicates a transapical approach of implanting a prosthetic heart valve, in this case to replace the mitral valve. In transapical delivery, a small incision is made between the ribs and into the apex of left ventricle 124 to deliver the prosthetic heart valve to the target site. A second dashed arrow, labeled "TS", indicates a transeptal approach of implanting a prosthetic heart valve in which the valve is passed through the septum between right atrium 112 and left atrium 122. Other percutaneous approaches for implanting a prosthetic heart valve are also contemplated herein.

Figure 2:
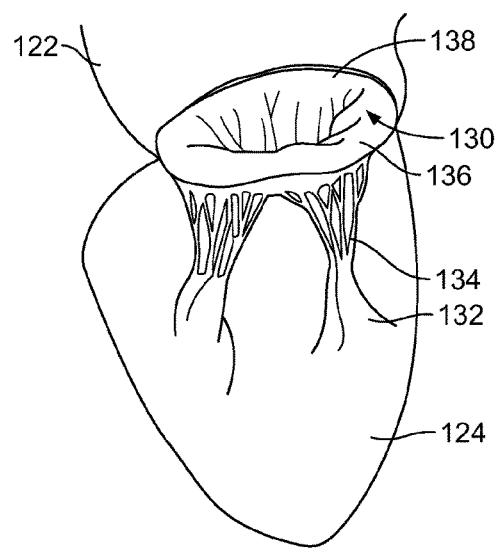
FIG. 2 is a schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cord-like tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower than that in left ventricle 124, leaflets 136, 138 attempt to evert to the low pressure regions. Chordae tendineae 134 prevent the eversion by becoming tense, thus pulling on leaflets 136, 138 and holding them in the closed position.

Figures 3A, 3B:
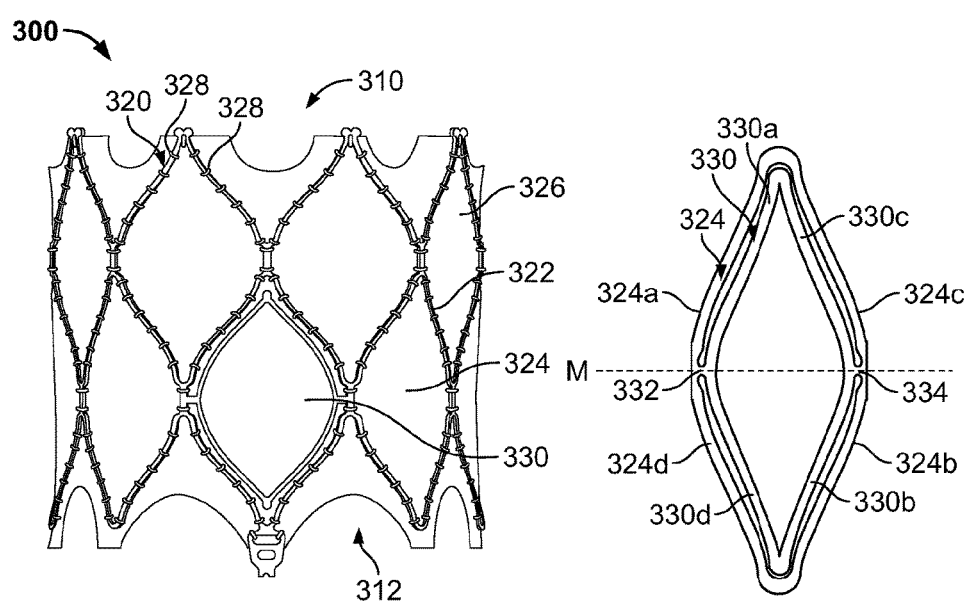
FIG. 3A is a partial front view of a prosthetic heart valve according to an embodiment of the disclosure.
FIG. 3B is an enlarged isolated front view of a nested cell in an expanded condition within another cell of the prosthetic heart valve of FIG. 3A.

FIG. 3A is a side view of prosthetic heart valve 300 in accordance with one embodiment of the present disclosure. FIG. 3A illustrates prosthetic heart valve 300 in a relaxed condition. Prosthetic heart valve 300 is a collapsible prosthetic heart valve designed to replace the function of the native mitral valve of a patient (see native mitral valve 130 of FIGS. 1-2). Generally, prosthetic valve 300 has inflow end 310 and outflow end 312. Prosthetic valve 300 may have a substantially cylindrical shape and may include features for anchoring it to native heart tissue, as will be discussed in more detail below. When used to replace native mitral valve 130, prosthetic valve 300 may have a low profile so as not to interfere with atrial function in the native valve annulus.

Prosthetic heart valve 300 may include stent 320, which may be formed from biocompatible materials that are capable of self-expansion, such as, for example, shape memory alloys including Nitinol. Stent 320 may include a plurality of struts 322 that form cells 324 connected to one another in one or more annular rows around the stent. Generally, cells 324 may all be of substantially the same size around the perimeter and along the length of stent 320. Alternatively, cells 324 near inflow end 310 may be larger than the cells near outflow end 312. Stent 320 may be expandable to provide a radial force to assist with positioning and stabilizing prosthetic heart valve 300 in the native valve annulus.

Prosthetic heart valve 300 may also include a generally cylindrical cuff 326 which may facilitate attachment of a valve assembly, described in more detail below, to stent 320. Cuff 326 may be attached to at least some struts 322, for example with sutures 328.

Figure 3D:
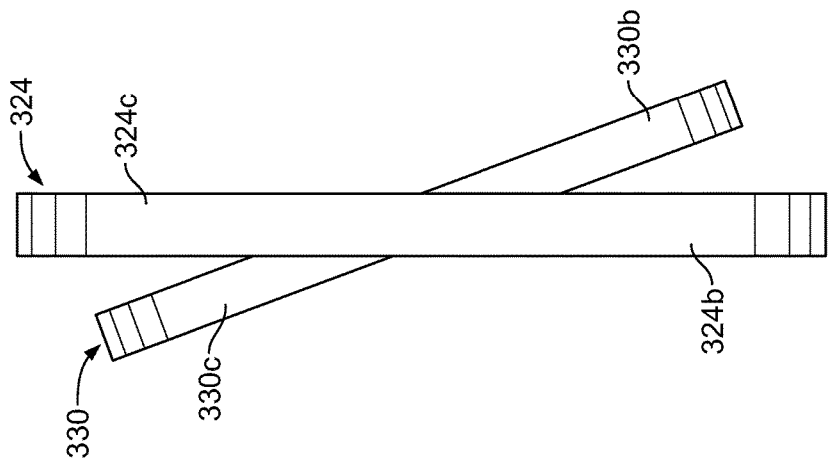
FIG. 3D is an enlarged isolated side view of the nested cell of FIG. 3B pivoted with respect to the other cell.
Figure 3C:
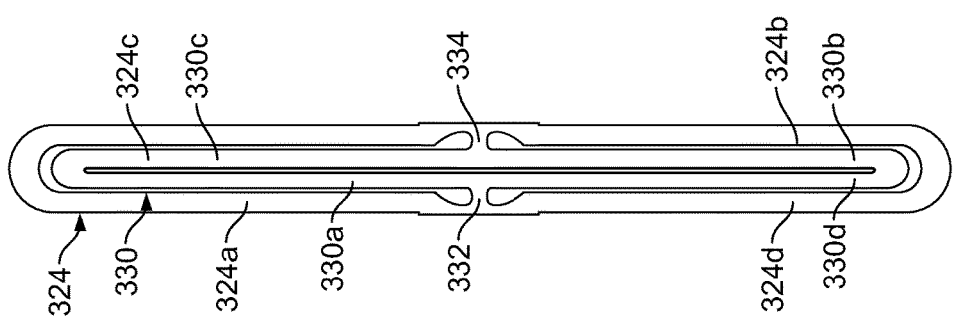
FIG. 3C is an enlarged isolated front view of the nested cell of FIG. 3B in a collapsed condition.

Stent 320 may include one or more nested cells 330. Nested cells 330 may facilitate the clamping of a native valve leaflet, such as posterior leaflet 136 and/or anterior leaflet 138 of mitral valve 130, upon implantation of prosthetic valve 300. One nested cell 330 is illustrated in greater detail in FIGS. 3B-D. In particular, FIGS. 3B-C illustrate cell 330 nested within a cell 324 of stent 320 in the expanded condition and the collapsed condition, respectively, with the remainder of prosthetic heart valve 300 omitted. In this embodiment, cell 324 may be thought of as being formed of four struts, including a first pair of generally parallel struts 324a-b and a second pair of generally parallel struts 324c-d. In the aggregate, struts 324a-d form generally a diamond shape when in the expanded condition. Nested cell 330 has a shape similar to cell 324, and may also be thought of as being formed of four struts 330a-d, with a first pair of generally parallel struts 330a-b and a second pair of generally parallel struts 330c-d that, in the aggregate, form generally a diamond shape when in the expanded condition. Cell 330, defined by struts 330a-d, is nested substantially within the perimeter of the struts 324a-d forming cell 324.

Nested cell 330 may be connected to cell 324 by connecting struts 332 and 334. Connecting struts 332 and 334 may each be relatively short struts that extend from cell 324 to nested cell 330 along a midline M of the cells. In this configuration, nested cell 330 may rotate or pivot about connecting struts 332 and 334 with respect to cell 324, as described below. For example, a side view of cell 324 and nested cell 330 in the collapsed condition is illustrated in FIG. 3D. Nested cell 330 is shown as rotated with respect to cell 324 about connecting struts 332 and 334 (not visible in FIG. 3D).

The ability of nested cell 330 to rotate with respect to cell 324, in combination with the shape memory property of stent 320, may help provide a number of different actions of nested cell 330 during delivery and deployment of prosthetic valve 300. For example, FIG. 4A illustrates nested cell 330, with cell 324 in phantom lines and the remainder of prosthetic heart valve 300 omitted. In this configuration, nested cell 330 is illustrated after it has been shape-set, for example by heat setting, so that struts 330d and 330b (strut 330d not visible in FIG. 4A) are angled radially outwardly with respect to struts 330a and 330c (strut 330a not visible in FIG. 4A). The term "angled radially outwardly" includes substantially straight flaring in the radially outward direction as well as a curved flaring in the radially outward direction. With this shape setting, nested cell 330 tends to revert to the illustrated condition when no external forces are applied to stent 320. One benefit of this particular configuration becomes clearer when viewed in the context of the use of a pair of nested cells 330 with a sheath 390 of a mitral valve delivery device.

FIG. 4B illustrates a longitudinal cross-sectional view of prosthetic heart valve 300 in the expanded condition. In this embodiment, prosthetic heart valve 300 may also include a substantially cylindrical valve assembly 360 including a pair of leaflets 362 and 364 attached to a cuff 326 (best illustrated in FIG. 3A). Leaflets 362 and 364 replace the function of native mitral valve leaflets 136 and 138 described above with reference to FIG. 2. That is, leaflets 362 and 364 coapt with one another to function as a one-way valve. Leaflets 362 and 364 may be wholly or partly formed of any suitable biological material, such as bovine or porcine pericardium, or polymers, such as polytetrafluoroethylene (PTFE), urethanes and the like. Stent 320 may include a pair of nested cells 330 substantially diametrically opposed to one another. Each of nested cells 330 is shape-set as described in connection with FIG. 4A. As illustrated in FIG. 4B, proximal struts 330b and 330d extend radially outwardly and proximally from stent 320. Distal struts 330a and 330c are substantially aligned within the cylindrical shape of stent 320, so that they are not readily visible in FIG. 4B.

FIG. 4C is a longitudinal cross-sectional view of prosthetic valve 300 in a collapsed condition and loaded into sheath 390 of a delivery device. Mitral valve delivery devices are known in the art and only sheath 390 is illustrated to facilitate the explanation of a function of nested cells 330. Sheath 390 may be in the form of a generally cylindrical tube extending from a proximal end (not illustrated) to a distal end 392. Although distal end 392 of sheath 390 is illustrated as an open end, additional structure would generally be provided along with the remainder of the delivery device to allow distal end 392 to be closed during delivery. During replacement of native mitral valve 130 with prosthetic valve 300, prosthetic valve 300 is first crimped or otherwise collapsed and secured near distal end 392 of sheath 390. Although a gap is shown between the outer diameter of prosthetic heart valve 300 and the inner diameter of sheath 390, this is meant to provide clarity and, in practice, some, if not all, of stent 320 of prosthetic heart valve 330 would be in direct contact with the inner surface of sheath 390. This contact restricts prosthetic heart valve 300 from expanding, while simultaneously causing nested cells 330 to be generally aligned with the outer circumference of stent 320. In other words, although proximal struts 330b and 330d of each nested cell 330 are shape-set to extend radially outwardly from stent 320, the inner diameter of sheath 390 constrains proximal struts 330b and 330d so that they generally align with the remainder of the collapsed stent. This constraint of proximal struts 330b and 300d creates a rotational stress in connecting struts 332 and 334. However, because nested cell 330 is constrained from rotating radially outwardly while within sheath 390, this rotational force on connecting struts 332 and 334 does not result in any significant movement of any of struts 330a-d.

During delivery of prosthetic valve 300, for example by a transapical route to native mitral valve 130, distal end 392 of the delivery device is advanced until it is near the site of implantation. Once positioned as desired, sheath 390 is retracted proximally relative to prosthetic heart valve 300, as illustrated in FIG. 4D. As the retraction of the sheath continues, more of prosthetic heart valve 300 is exposed, reducing the constraint caused by the sheath. As this constraint is reduced or released, stent 320 begins to revert to its shape-set expanded condition (not shown in FIG. 4D). As distal, end 392 of sheath 390 begins to retract proximally past nested cells 330, the stored rotational stress in connecting struts 332 and 334 causes distal struts 330a and 330c to rotate radially outwardly about connecting struts 332 and 334. This motion releases the stored rotational stress and creates a rotational stress in the opposite direction in connecting struts 332 and 334. Additionally, the outward rotation of distal struts 330a and 330c creates a clearance space between the distal struts and the outer perimeter of the remainder of stent 320. During deployment of prosthetic heart valve 300 within the annulus of native mitral valve 130, prosthetic heart valve 300 may be positioned relative to the native mitral valve such that posterior leaflet 136 and anterior leaflet 138 of mitral valve 130 are each positioned in one of these clearance spaces. For example, this may be accomplished by advancing prosthetic heart valve 300 distally once the clearance space has been created. As sheath 390 is retracted further proximally beyond the remainder of nested cells 330, the stored rotational stress in connecting struts 332 and 334 causes nested cells 330 to attempt to revert back to the shape-set configuration illustrated in FIG. 4A.

Figure 4E:
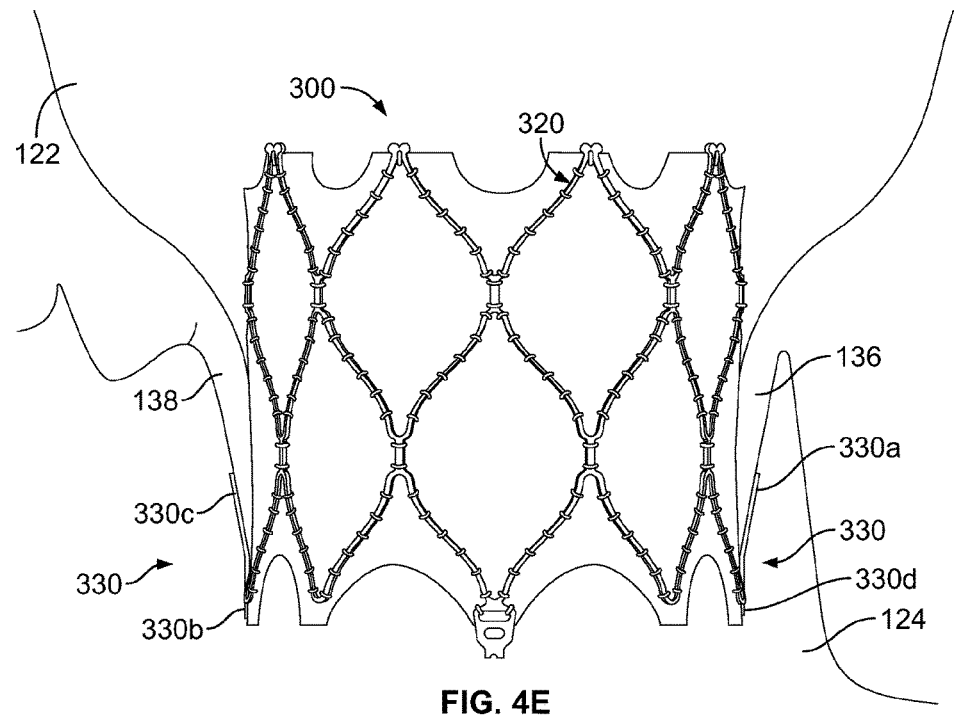
FIG. 4E is a partial schematic representation of the prosthetic heart valve of FIG. 4B disposed in a native valve annulus.

If prosthetic valve 300 is positioned properly, as nested cells 330 attempt to revert back to their original shape-set configuration, posterior leaflet 136 will be clamped between stent 320 and distal struts 330a and 330c of one of the nested cells and anterior leaflet 138 will be clamped between stent 320 and the distal struts of the other nested cell, as illustrated in FIG. 4E. It should be noted that, if not positioned properly, prosthetic heart valve 300 may be resheathed into sheath 390 as long as nested cells 330 have not been fully exposed. If nested cells 330 were fully exposed, proximal struts 330b and 330d of each nested cell would protrude radially outwardly, interfering with the ability of stent 320 to retract back into sheath 390. Rather, distal end 392 of sheath 390 would catch on protruding proximal struts 330b and 330d. The above-described clamping mechanism may provide a sturdy securement of prosthetic heart valve 300 to native mitral valve 130. Other known mechanisms for securing a prosthetic valve to a native valve may provide less robust connections, which may result in relative motion between the prosthetic valve and the native valve during in vivo operation, particularly during the time period prior to tissue ingrowth. The above-described clamping mechanism, on the other hand, may reduce or eliminate relative motion between prosthetic heart valve 300 and native mitral valve 130 from the moment of implantation.

Figure 4F:
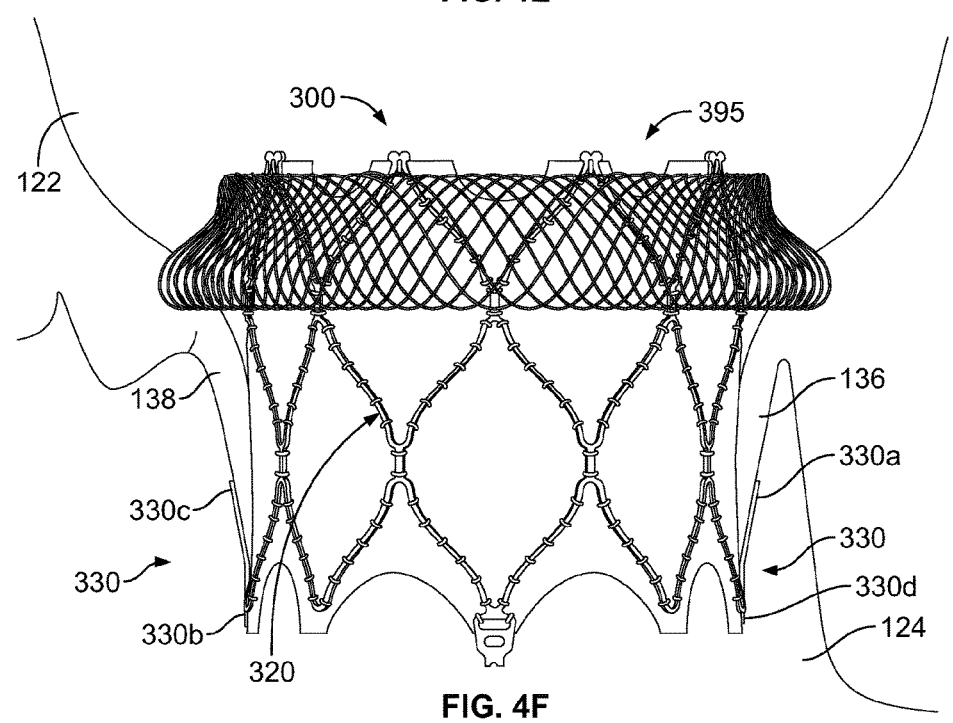
FIG. 4F is a partial schematic representation of another embodiment of a prosthetic heart valve disposed in an native valve annulus.

A number of other components known for use with prosthetic valves may be provided but have not been illustrated herein for clarity. For example, the embodiment of prosthetic valve 300 described above for use in replacement of native mitral valve 130 may include a braided seal 395, illustrated in FIG. 4F, that facilitates holding prosthetic valve 300 on the atrial side of the mitral valve annulus. This and other types of braided stents are described more fully in, for example, U.S. Provisional Patent Application No. 61/836,427 titled "ANCHORED MITRAL VALVE PROSTHESIS," filed on Jun. 18, 2013.

Similarly, a number of variations of the components described above are still within the scope of the present disclosure. For example, although a prosthetic heart valve has been described with two nested cells on substantially diametrically opposite portions of the prosthetic valve, more or fewer nested cells may be provided. For example, one, three, four or more nested cells may be used as desired. Generally, it may be useful to use a number of nested cells at least equal to the number of leaflets in the native valve to be replaced. For example, at least three nested cells may be particularly useful for a prosthetic heart valve that is to replace a tricuspid or aortic valve. However, it should be understood that any number of nested cells may be appropriate for a valve with any number of native leaflets, and the nested cells need not be equally spaced around the circumference of the prosthetic valve. Further, although struts of the nested cell are described as "angled" radially outward, this also includes a configuration in which struts are curved outwardly. An outward curve may be less likely to dig into an inner wall of a delivery device when the stent is in the collapsed condition compared to a straight angle. For example, a small or slight curve at the end of a nested cell may reduce the tendency of the nested cell to dig into the delivery device during delivery, and may also help minimize deployment forces.

A partial cell 430 nested within a cell 424 of a prosthetic heart valve 400 in the expanded condition is illustrated in FIG. 5A. In FIG. 5A, only cell 424 and nested partial cell 430 are illustrated. In this embodiment, as in prosthetic heart valve 300, cell 424 may be thought of as being formed of four struts, including a first pair of generally parallel struts 424a-b and a second pair of generally parallel struts 424c-d. In the aggregate, struts 424a-d form generally a diamond shape when in the expanded condition. Nested partial cell 430, however, takes the form of a half or partial cell, generally following a shape similar to the upper or distal half of cell 424. Nested partial cell 430 may be thought of as being formed of two struts 430a and 430c that, in the aggregate, form generally a half or partial diamond shape when in the expanded condition. As in prosthetic heart valve 300, nested partial cell 430 may be connected to cell 424 by connecting struts 432 and 434. In this configuration, nested partial cell 430 may rotate or pivot about connecting struts 432 and 434 with respect to cell 424. In addition, nested partial cell 430 may include a through hole, such as an aperture or eyelet 435. Eyelet 435 may be positioned at a distal end of nested partial cell 430 where strut 430a meets strut 430c, but other positioning may be acceptable. As is described below, in certain embodiments, eyelet 435 enables a user to manipulate nested partial cell 430 during valve deployment.

FIG. 5B illustrates nested partial cell 430 after it has been shape-set in one particular configuration with cell 424 in phantom lines and the remainder of prosthetic heart valve 400 omitted. In this configuration, distal struts 430a and 430c (strut 430a not visible in FIG. 5B) are angled radially inwardly with respect to cell 424. With this shape setting, nested partial cell 430 tends to revert to the illustrated condition when no external forces are applied.

Figure 5E:
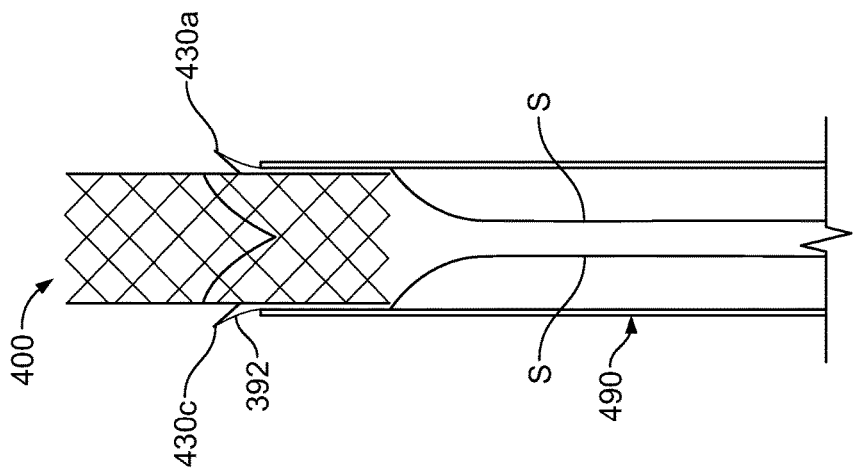
FIG. 5E is a longitudinal cross-section of the prosthetic heart valve of FIG. 5C being deployed from the delivery device.
Figure 5D:
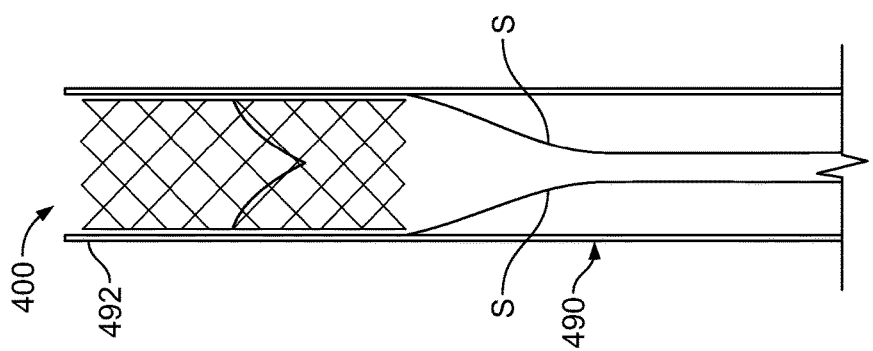
FIG. 5D is a longitudinal cross-section of the prosthetic heart valve of FIG. 5C in a collapsed condition within a delivery device.
Figure 5C:
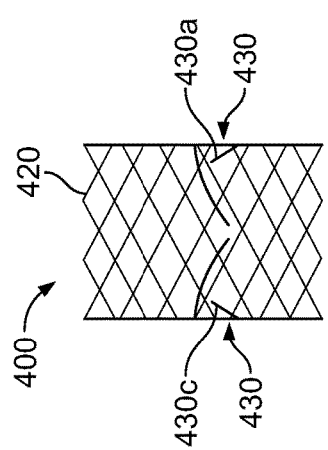
FIG. 5C is a longitudinal cross-section a prosthetic heart valve incorporating the nested cell of FIG. 5A in an expanded condition.

FIG. 5C illustrates a longitudinal cross-sectional view of prosthetic heart valve 400 in the expanded condition. Prosthetic heart valve 400 may be the same as prosthetic heart valve 300 in all respects other than nested partial cells 430. Stent 420 of prosthetic heart valve 400 may include a pair of nested partial cells 430 substantially diametrically opposed to one another. Nested partial cells 430 are each shape-set as described in connection with FIG. 5B. As illustrated in FIG. 5C, distal struts 430a and 430c extend radially inwardly and distally from stent 420.

FIG. 5D is a longitudinal cross-sectional view of prosthetic valve 400 in a collapsed condition and loaded into sheath 490 of a delivery device. Sheath 490 may be substantially the same as sheath 390, having the form of a generally cylindrical tube extending from a proximal end (not illustrated) to a distal end 492. The delivery system may also include one or more connectors, such as pull wires or sutures S, connected to eyelets 435 (see FIG. 5A) of nested partial cells 430. Each suture S may be threaded through a corresponding eyelet 435 to form a loop at the distal end of each nested partial cell 430 with two strands of the suture extending proximally through sheath 490. Sutures S may extend proximally, preferably between the outer circumference of prosthetic valve 400 and the inner circumference of sheath 490, so that their proximal ends are positioned outside the patient for manipulation by the user. Although sutures S are illustrated as freely extending proximally, it should be understood that other structures, such as guide lumens, may be used in conjunction with sutures S. In a variant hereof, partial cell 430 may not be provided with any eyelets 435. In such variant, a length of suture S may be looped around one or more of struts 430a and 430c at the distal end of partial cell 430, with the two strands of the suture extending proximally through sheath 490.

As prosthetic valve 400 is deployed, typically by retracting sheath 490, nested partial cells 430 become clear of the constraint of sheath 490. Once nested partial cells 430 are clear of sheath 490, the user may manipulate sutures S, for example by manually pulling them proximally, to cause nested partial cells 430, and particularly distal struts 430a and 430c, to open radially outwardly, as shown in FIG. 5E, creating clearance spaces between the distal struts and the outer perimeter of the remainder of stent 420. As described in relation to previous embodiments, once nested partial cells 430 extend radially outwardly, prosthetic heart valve 400 may be positioned so that posterior leaflet 136 and anterior leaflet 138 of native mitral valve 130 are each positioned in one of these clearance spaces. Once in the desired position, the user may release tension on sutures S so that distal struts 430a and 430c begin to revert to their radially inwardly extending shape-set position. If prosthetic valve 400 is positioned properly, posterior leaflet 136 will be clamped between stent 420 and distal struts 430a and 430c of one of the nested partial cells and anterior leaflet 138 will be clamped between stent 420 and the distal struts of the other nested partial.

It should be noted that, if prosthetic valve 400 is not positioned properly, the user may again pull sutures S proximally to move distal struts 430a and 430c radially outwardly so that the prosthetic heart valve may be repositioned. As long as sutures S are connected to nested partial cells 430 and prosthetic heart valve 400 has not been entirely released from sheath 490, prosthetic heart valve 400 may be resheathed if desired. Once nested partial cells 430 are clamped in a desired position, the user may pull one strand of each suture S proximally to remove sutures S from the patient.

It should be understood that variations may be made to prosthetic heart valve 400 described above. For example, although distal struts 430a and 430c are described as being shape-set so that they tend to bend radially inwardly, other shape-setting may also function suitably. For example, distal struts 430a and 430c may be shape-set so that they generally align within the cylindrical shape of stent 420 when no force is applied. Also, eyelet 435 may be replaced with other structures that may provide similar functionality. For example, struts 430a and/or 430c may have ridges, flanges, extensions, or other structures around which sutures S are wrapped. However, eyelet 435 may provide for a more secure connection to sutures S than these alternatives. Additionally, although sutures S are described as being manipulated manually by a user, sutures S may be connected at their proximal ends to other structures, such as a sliding mechanism in a handle of the delivery device, to facilitate proximal and distal movement of sutures S. Similarly, sutures S may be attached to nested partial cells 430 without the use of an eyelet 435. Still further, a full cell, such as cell 330 described in connection to FIG. 3B, may be used with an eyelet in a similar fashion as described in connection to nested partial cell 430.

Figure 6C:
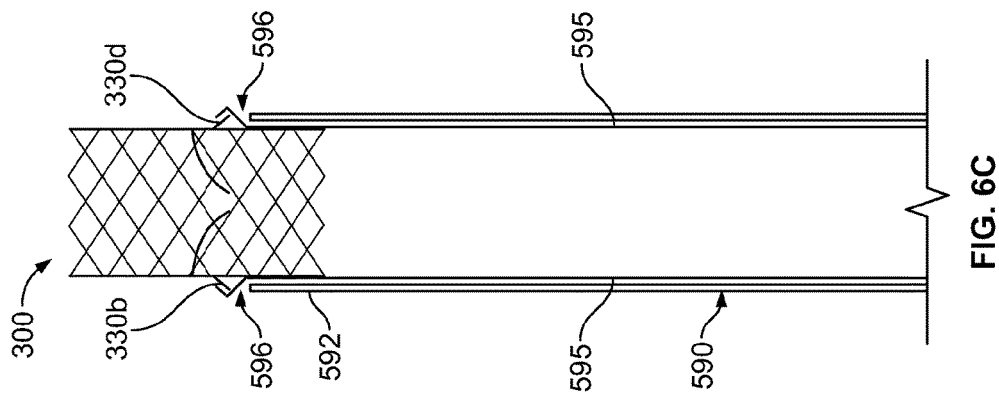
FIG. 6C is a longitudinal cross-section of the prosthetic heart valve of FIG. 6A partially within the delivery device of FIG. 6A with the resheathing member in an extended position.
Figure 6B:
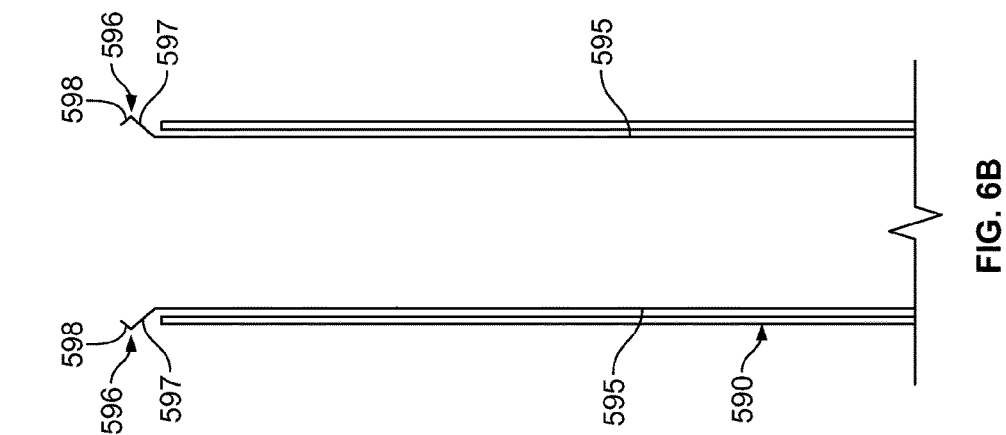
FIG. 6B is a longitudinal cross-section of the delivery device of FIG. 6A with a resheathing member in an extended position.
Figure 6A:
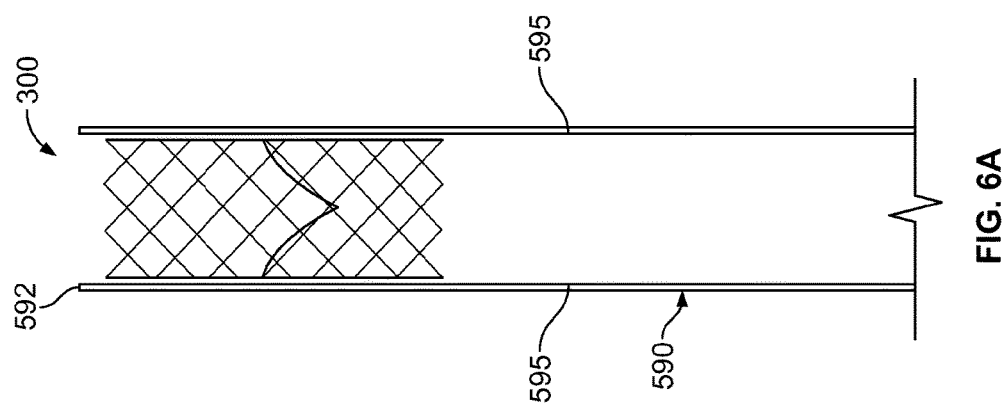
FIG. 6A is a longitudinal cross-section of a prosthetic heart valve in a collapsed condition within a delivery device according to another embodiment of the disclosure.

FIG. 6A is a longitudinal cross-sectional view of prosthetic valve 300 in a collapsed condition and loaded into sheath 590 of a delivery device. Prosthetic valve 300 is the same as that described in connection with FIGS. 3A-4B and with nested cells 330 shape-set as described in connection with FIG. 4A. Sheath 590 may be substantially the same as sheaths 390 and 490, having the form of a generally cylindrical tube extending from a proximal end (not illustrated) to a distal end 592. The delivery system may also include one or more resheathing members, such as arms 595. Each arm 595 may extend from the proximal end of sheath 590 toward distal end 592. In FIG. 6A, arms 595 are illustrated in a proximal or retracted condition in which a distal end of each arm is positioned within sheath 590, preferably between the outer circumference of prosthetic valve 300 and the inner circumference of sheath 590. The proximal end of each arm 595 may extend far enough proximally to be positioned outside the patient's body so that a user may manipulate each arm 595, for example by pushing or pulling the arm. The arms 595 may alternately be connected to a handle or other portion of the delivery device to facilitate manipulation of the arms.

The structure of arms 595 is best illustrated in FIG. 6B, which illustrates sheath 590 with arms 595 in a distal or extended condition, with prosthetic valve 300 omitted from the figure. Arms 595 may be transitioned from the retracted condition shown in FIG. 6A to the extended condition shown in FIG. 6B by proximal movement of sheath 590 relative to arms 595, for example by retraction of sheath 590 with respect to arms 595. The distal portion 596 of each arm 595 may include an outwardly flared segment 597 with a finger 598 canted radially inward at its distal end. Each arm 595 may be formed of a shape-memory alloy such as Nitinol shape-set such that distal portion 596 takes the illustrated shape upon transitioning to the extended condition. While arms 595 take this shape when in the extended condition, arms 595, including distal portion 596, are substantially linear when in the retracted condition.

The function of arms 595 is best illustrated with respect to FIG. 6C, which shows sheath 590 with arms 595 in the extended condition along with prosthetic valve 300 in a partially expanded condition. In particular, sheath 590 has been retracted such that prosthetic valve 300 takes a similar form as illustrated in FIG. 4B, with proximal struts 330b and 330d having already cleared distal end 592 of sheath 590. However, unlike the fully expanded condition illustrated in FIG. 4B, prosthetic valve 300 is only partially expanded in FIG. 6C. At this point, if prosthetic valve 300 is positioned properly, distal struts 330a and 330c of each nested cell 330 will have clamped one of the native mitral valve leaflets. If the position is satisfactory, the user may withdraw arms 595 until the distal portion 596 of each arm is positioned within sheath 590, at which point the delivery device may be removed from the patient. However, if the position of prosthetic valve 300 is not satisfactory, the user may advance sheath 590 distally with respect to prosthetic valve 300, keeping arms 595 stationary relative to the prosthetic valve. As sheath 590 advances distally, it compresses or flattens flared segments 597 and fingers 598 of arms 595 inwardly, which in turn causes proximal struts 330b and 330d of nested cells 330 to compress inwardly toward the remainder of stent 320. Once sheath 590 surrounds proximal struts 330b and 330d, the clamping action of distal struts 330a and 330c on the native mitral valve leaflets will be released, allowing the user to reposition prosthetic heart valve 300 as desired.

FIG. 7A is a longitudinal cross-sectional view of prosthetic heart valve 300 in the expanded condition along with a position controlling component, with nested cells 330 shape-set as described in connection with FIG. 4A. The position controlling component may be in the form of a band 600, for example. Band 600 may be a strip of material, such as a fabric or a shape-memory alloy, that encircles prosthetic heart valve 300. In particular, band 600 may be positioned at or close to the point at which distal struts 330a and 330c of nested cells 330 transition to proximal struts 330d and 330b, respectively. In other words, band 600 may be positioned such that it extends generally across midline M of nested cells 330 and connecting struts 332 and 334 (FIG. 3B) which act as pivot points for nested cells 330.

Band 600 may include one, two, or more connectors 610. Connectors 610 may be push/pull wires having sufficient strength and stiffness to transmit force to band 600 in both a pulling (proximal) and pushing (distal) direction. Each connector 610 has a distal end operatively attached to band 600, a proximal end (not illustrated), and a length such that, when prosthetic heart valve 300 is at the site of implantation, the proximal end of each connector 610 lies outside the patient's body and may be manipulated by the user. The proximal end of each connector 610 may be free for manual manipulation, or attached to a handle or other portion of the delivery device, such as a slider, to facilitate manipulation of connectors 610. The distal ends of each connector 610 may be threaded, for example, with a corresponding connector portion on band 600 also being threaded.

The delivery of prosthetic valve 300 with band 600 may be accomplished mostly identically to the procedure described in connection with FIGS. 4C-E. During delivery of prosthetic valve 300, band 600 is in a first position, at or close to the point at which distal struts 330a and 330c of nested cells 330 transition to proximal struts 330d and 330b, respectively. Band 600 may alternately encircle proximal struts 330b and 330d in the first position. As the sheath of the delivery device is retracted proximally relative to prosthetic valve 300, the prosthetic valve begins to expand to its circumferential shape. Band 600 will also begin to take a circumferential shape, either by self-expansion or due to expansion of prosthetic heart valve 300 which the band encircles.

After prosthetic valve 300 has been partially released from a sheath (not illustrated in FIG. 7A), such that a portion of prosthetic valve 300 remains within the sheath but nested cells 330 are clear of the sheath, distal struts 330a and 330c extend radially outwardly, as illustrated in FIG. 7A. This is possible because band 600 encircles proximal struts 330b and 330d, causing the distal struts to be pivoted outwardly. If positioned properly, at this point the native mitral valve leaflets are positioned within the gap between distal struts 330b, 330d, and the remainder of prosthetic heart valve 300. The user may then advance band 600 distally with respect to stent 320 using connectors 610. As band 600 advances distally to a second position, it encircles distal struts 300a and 330c, causing them to pivot inwardly and clamp the native leaflets, as shown in FIG. 7B.

If at this point the positioning of prosthetic heart valve 300 is not to the user's satisfaction, the user may pull connectors 610 proximally, resulting in the proximal movement of band 600 back to the first position. As band 600 moves proximally relative to prosthetic heart valve 300, it forces proximal struts 330d and 330b radially inwardly, which in turn causes distal struts 330a and 330c to pivot radially outwardly, releasing the clamping force on the native mitral valve leaflets. Then, prosthetic heart valve 300 may be resheathed, and deployment of prosthetic valve 300 may be attempted again. Once a satisfactory deployment has been completed, the user may unscrew connectors 610 from band 600 by rotating them. Once disconnected, connectors 610 and the remainder of the delivery system may be removed from the patient, leaving prosthetic heart valve 300, along with band 600, permanently implanted in the patient.

Although nested cells 330 and 430 have been described above with respect to particular configurations, it should be understood that other configurations are within the scope of this disclosure. For example, FIGS. 8A-B illustrate an alternate embodiment of a cell 330' nested within cell 324 of stent 320 in the expanded condition and the collapsed condition, respectively, with the remainder of prosthetic heart valve 300 omitted for clarity. In this embodiment, proximal struts 330b' and 330d' connect to cell 324 at connection points 332' and 334', respectively. Connection points 332' and 334' may be thicker than connection points 332 and 334 of nested cell 330. For connection points 332 and 334 to act as pivot points, the material forming the connection points may need to be relatively thin to allow for the requisite twisting of the connection points. However, this twisting may create a relatively large amount of torsion and/or stress on connection points 332 and 334, which may be undesirable. Connection points 332' and 334' may be thicker to reduce the torsion and/or stresses on the connection points, but this may also reduce or eliminate the ability of connection points 332' and 334' to twist to create the pivoting motion described in connection to cell 330'. As is described in greater detail below, a pivoting or rocking motion can be achieved with thick connection points 332' and 334' by attaching distal struts 330a' and 330c' directly to proximal struts 330d' and 330b', respectively, rather than to connection points 332' and 334'.

As noted above, proximal strut 330d' connects to distal strut 330a' at first connection point 333' spaced proximally of connection point 332', while proximal strut 330b' connects to distal strut 330c' at second connection point 335' spaced proximally of connection point 334'. Once shape-set, for example in a similar manner as described in connection with FIG. 4A, radially inward pivoting or compression of proximal struts 330b' and 330d' cause those struts to rotate, or pivot, about connection points 332' and 334'. However, because of the thickness of connection points 332' and 334', they experience relatively little twisting and low stresses. Further, as proximal struts 330b' and 330d' are compressed or pivoted radially inwardly, first connection point 333' and second connection point 335' also move toward the plane of cell 324. Because distal struts 330a' and 330c' extend from first connection point 333' and second connection point 335', respectively, distal struts 330a' and 330c' rotate radially outward from the plane of cell 324 as proximal struts 330b' and 330c' move toward the plane of cell 324. This motion is illustrated in FIGS. 8C-E.

Figure 8E:
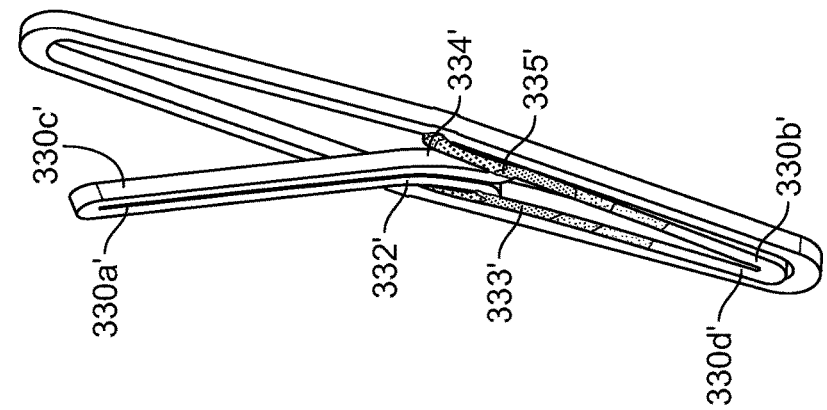
FIGS. 8C-E are enlarged isolated perspective views of the nested cell of FIG. 8A in different stages of pivoting with respect to the other cell of the prosthetic heart valve in the collapsed condition.
Figure 8D:
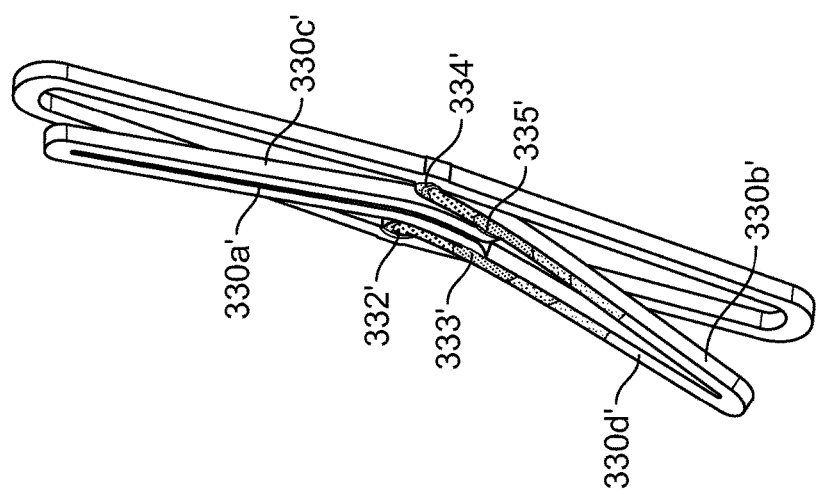
Figure 8C:
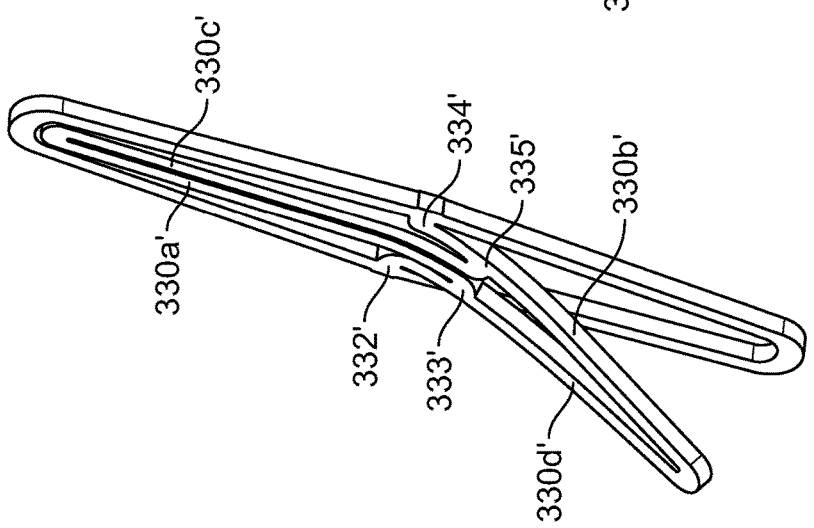

In the particular embodiment illustrated in FIGS. 8A-E, distal struts 330a' and 330c' may be capable of rotating or pivoting a relatively large distance from the plane of cell 324. By moving connection points 333' and 335' proximally of connection points 332' and 334', proximal struts 330b' and 330d' may be shorter in the axial or length direction than distal struts 330a' and 330c', without significantly affecting the shape of cell 324. In other words, connection points 332' and 334' are positioned substantially at the midline of cell 324, while the connection points 333' and 335' are axially offset from the connection points 332' and 334'. As illustrated in FIG. 8B, when in the collapsed condition, proximal struts 330b' and 330d' have an axial length of $L_2$ which is less than the axial length $L_1$ of distal struts 330a' and 330c'.

As noted above, proximal struts 330b' and 330d' may be shape-set such that, in the absence of applied force, they each extend radially outwardly from prosthetic heart valve 300. Distal struts 330a' and 330c' may be shape-set such that, in the absence of applied force, they each generally align within the cylindrical shape of stent 320. During deployment of prosthetic valve 300 in a manner similar or identical to that described in connection with FIGS. 4C-E, the smaller axial length $L_2$ of proximal struts 330b' and 330d' compared to the axial length $L_1$ of distal struts 330a' and 330c' may provide a greater amount of pivoting than might be seen if the axial length of the proximal struts and distal struts were equal. This additional pivoting motion may facilitate clamping of the native mitral valves.

Figure 9:
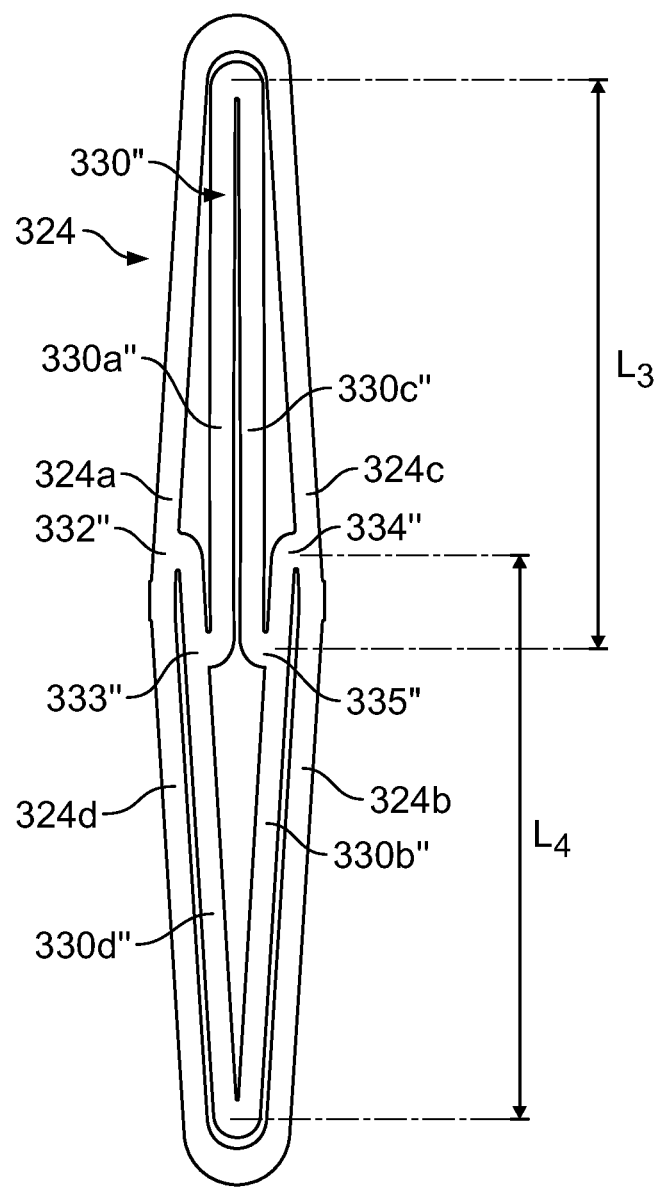
FIG. 9 is an enlarged isolated front view of another embodiment of a nested cell in a collapsed condition within another cell of a prosthetic heart valve.

It should be understood that, when using relatively thick connection points between a first cell and a second cell nested within the first cell, the configuration may vary from that described in connection with FIGS. 8A-E. For example, FIG. 9 illustrates another embodiment of a cell 330" nested within cell 324 in a collapsed configuration. Nested cell 330" is similar to nested cell 330' in a number of ways. For example, distal strut 330a" connects to proximal strut 330d" at first connection point 333", while distal strut 330c" connects to proximal strut 330b" at second connection point 335". Further, proximal strut 330d" connects to cell 324 at connection point 332" and proximal strut 330b" connects to cell 324 at connection point 334". However, in this embodiment, connection points 332" and 334" are not positioned substantially at the midline of cell 324, but are rather connected to proximal struts 324a and 324c, respectively. In this configuration, proximal struts 330b" and 330d" have an axial length $L_4$ that is substantially the same as the axial length $L_3$ of distal struts 330a" and 33c". As should be apparent, a variety of configurations may be possible to suit a particular purpose without deviating from the concepts disclosed herein.

According to one embodiment of the disclosure, a collapsible and expandable stent extending in an axial direction from a proximal end to a distal end comprises: a plurality of first cells, each first cell having an open space defined by a first plurality of struts; a second cell nested in the open space of one of the first cells, the second cell being defined by a second plurality of struts; and first and second connecting struts connecting the second cell to the one of the first cells; wherein the second cell is configured to pivot about the first and second connecting struts with respect to the one of the first cells; and/or a pulling member operably connected to at least one of the second plurality of struts; and/or an aperture in the at least one of the second plurality of struts, the pulling member being threaded through the aperture; and/or the second plurality of struts includes a first strut, a second strut, a third strut, and a fourth strut, the first and second struts each being positioned closer to the proximal end of the stent than the third and fourth struts; and/or the first strut is connected to the third strut at a first connection point and the second strut is connected to the fourth strut at a second connection point, the first and second connection points being offset in the axial direction from the first and second connecting struts; and/or the first and second struts each has a length in the axial direction which is smaller than a length in the axial direction of each of the third and fourth struts; and/or the second plurality of struts includes a first strut, a second strut, a third strut, and a fourth strut, the first strut being connected to the first cell via the first connecting strut, the second strut being connected to the first strut and being connected to the first cell via the second connecting strut, the third strut being connected to the first strut, and the fourth strut being connected to the third strut and to the second strut; and/or the one of the first cells defines a surface and the second cell includes first and second struts that do not lie within the surface when no external force is applied to the stent; and/or the second cell includes third and fourth struts that lie within the surface when no external force is applied to the stent; and/or a band applied about a circumference of the stent and movable relative to the stent in the axial direction and a pull wire operably connected to the band; and/or the pull wire is threadedly connected to the band; and/or the pull wire is operable to transmit force to the band to move the band relative to the stent in a proximal axial direction and in a distal axial direction; and/or a prosthetic heart valve may comprise the above-described collapsible and expandable stent and a collapsible and expandable valve assembly disposed within the stent and having a plurality of leaflets.

According to another embodiment of the disclosure, a method of delivering a prosthetic heart valve into a patient comprises: loading the prosthetic heart valve into a delivery device in a collapsed condition, the delivery device including a sheath extending from a proximal end to a distal end, the prosthetic heart valve including a stent extending in an axial direction from a proximal end to a distal end and having a plurality of first cells, each first cell having an open space defined by a first plurality of struts, and a second cell nested in the open space of one of the first cells, the second cell being defined by a second plurality of struts; advancing the sheath to an implant site within the patient; retracting the sheath with respect to the prosthetic heart valve until at least a portion of the second cell is positioned outside of the sheath; and pivoting the second cell with respect to the one of the first cells to create a clearance space between the second cell and an outer perimeter of the stent; and/or the pivoting step includes proximally pulling a pulling member operably connected to at least one of the second plurality of struts; and/or the one of the first cells defines a surface and the second cell includes first and second struts that do not lie within the surface when no force is applied to the stent; and/or the second cell includes third and fourth struts that lie within the surface when no force is applied to the stent; and/or the step pivoting step includes retracting the sheath with respect to the prosthetic heart valve until at least a portion of the third and fourth struts is positioned outside of the sheath and at least a portion of the first and second struts is covered by the sheath; and/or the prosthetic heart valve includes a band encircling the stent and a pull wire operably connected to the band; and/or after the pivoting step, retracting the band relative to the stent in a proximal axial direction by pulling the pull wire proximally until the band overlies the first and second struts, but not the third and fourth struts, to pivot the second cell with respect to the first cell; and/or advancing the prosthetic heart valve distally after the clearance space has been created between the second cell and the outer perimeter of the stent until at least a portion of a native valve structure is positioned within the clearance space; and pivoting the second cell with respect to the first cell to clamp the portion of the native valve structure between the second cell and the first cell.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A collapsible and expandable stent extending in an axial direction from an outflow end to an inflow end, comprising:
   a plurality of first cells, each first cell having an open space defined by a first plurality of struts;
   a second cell nested in the open space of one of the first cells, the second cell being defined by a second plurality of struts; and
   first and second connecting struts connecting the second cell to the one of the first cells;
   wherein the second cell is configured to pivot about the first and second connecting struts with respect to the one of the first cells,
   wherein the one of the first cells defines a surface, and the second cell includes first and second struts meeting at a first apex that does not lie within the surface when no external force is applied to the stent, and the second cell includes third and fourth struts meeting at a second apex that does lie within the surface when no external force is applied to the stent, the first and second apices each configured to pivot into and out of the surface.

2. The stent of claim 1, further comprising a pulling member operably connected to at least one of the second plurality of struts.

3. The stent of claim 2, further comprising an aperture in the at least one of the second plurality of struts, the pulling member being threaded through the aperture.

4. The stent of claim 1, wherein the first and second struts are each positioned closer to the outflow end of the stent than are the third and fourth struts.

5. The stent of claim 4, wherein the first strut is connected to the third strut at a first connection point and the second strut is connected to the fourth strut at a second connection point, the first and second connection points being offset in the axial direction from the first and second connecting struts.

6. The stent of claim 5, wherein the first and second struts each has a length in the axial direction which is smaller than a length in the axial direction of each of the third and fourth struts.

7. The stent of claim 1, wherein the first strut of the second cell is connected to the first cell via the first connecting strut, the second strut of the second cell is connected to the first strut and is connected to the first cell via the second connecting strut, the third strut of the second cell is connected to the first strut, and the fourth strut of the second cell is connected to the third strut and to the second strut.

8. The stent of claim 1, further comprising:
   a band applied about a circumference of the stent and movable relative to the stent in the axial direction; and
   a pull wire operably connected to the band.

9. The stent of claim 8, wherein the pull wire is threadedly connected to the band.

10. The stent of claim 8, wherein the pull wire is operable to transmit force to the band to move the band relative to the stent in a proximal axial direction and in a distal axial direction.

11. The stent of claim 1, further comprising a collapsible and expandable valve assembly disposed within the stent and having a plurality of leaflets.

* * * * *